United States Patent [19]

Lerner et al.

[11] Patent Number: 4,564,597

[45] Date of Patent: Jan. 14, 1986

[54] ANTI-SM HYBRIDOMA

[75] Inventors: Ethan A. Lerner; Michael R. Lerner, both of New Haven, Conn.

[73] Assignee: Research Corporation, New York, N.Y.

[21] Appl. No.: 244,899

[22] Filed: Mar. 18, 1981

[51] Int. Cl.$^4$ .................... G01N 33/54; G01N 33/56; C12N 5/00

[52] U.S. Cl. .......................................... 435/7; 435/6; 435/68; 435/172.2; 435/188; 435/240; 435/948; 436/536; 436/508; 436/537; 436/542; 436/548; 436/80; 436/804; 436/811; 436/815; 260/112 R; 424/1.1; 424/85

[58] Field of Search ..................... 23/230 B, 915, 920; 435/7, 948, 240, 4, 67, 68, 70, 172.2, 188; 424/1, 1.5, 85-89, 93, 1.1, 177; 436/506, 508, 536-548, 800, 811, 815, 804; 260/112 R; 935/95, 104, 110

[56] References Cited

U.S. PATENT DOCUMENTS

| 4,024,235 | 5/1977 | Weetall et al. | 424/1 |
|---|---|---|---|
| 4,196,265 | 4/1980 | Koprowski et al. | 435/2 |

OTHER PUBLICATIONS

Eilat, D. et al., Molecular Immunology, vol. 18(7), pp. 589-595, (1981).
Eilat, D. et al., J. of Immunology, vol. 124(2), pp. 766-768, (1980).
Galfre, G. et al., Methods in Enzymology, vol. 73, pp. 1-45, (1981), Langone, J. J. ed., Academic Press, N.Y.
Goodman, S. A., National Library of Medicine Literature Search, "Lymphocyte Hybridomas through 12-1980)".
Lerner, M. R. et al., Proc. Natl. Acad. Sci., USA, vol. 78, (2), pp. 805-809, (1981).
Lerner, E. A. et al., Proc. Natl. Acad. Sci., USA, vol. 78, (5), pp. 2737-2741, (May 1981), not prior art.
Lerner, M. R. et al., Cell, vol. 25(2), pp. 298-300, (1981).
Pisetoky, D. S. et al., J. Immunology, vol. 129(4), pp. 1489-1492, (1982), not prior art.
Lerner, M. R. et al., Nature, vol. 283 (5743), pp. 220-224, (1980).
Barque, J. P. et al., Biochem. Biophys. Res. Commun., vol. 99(10), pp. 284-291, (1981).
Lerner, M. R. et al., Science, vol. 211 (4480), pp. 400-402, (1981).
Lerner, M. R. et al., Genet. Evol. RNA Polymerase, TRNA Ribosomes, pp. 299-311, (1980), Univ. Tokyo, Tokyo, Osawa, S. ed.
J. Exp. Med., vol. 147, (1978), pp. 582-587, R. A. Eisenberg et al.
Proc. Natl. Acad. Sci. USA, vol. 76, No. 11, (1979), pp. 5495-5499, M. R. Lerner and J. A. Steitz, see p. 5499, col. 1, lines 5-27.
J. Immunol., vol. 124(2), (1980), pp. 766-768, Eilat, D. et al., (abstract mailed).

Primary Examiner—Thomas G. Wiseman
Assistant Examiner—M. Moskowitz
Attorney, Agent, or Firm—Scully, Scott, Murphy & Presser

[57] ABSTRACT

Anti-Sm antibodies are produced by the hybridoma technique and employed to test for lupus erythematosus in humans.

11 Claims, No Drawings

ANTI-SM HYBRIDOMA

The invention described herein was made in the course of work under a grant or award from the Department of Health and Human Services.

This invention relates to monoclonal anti-Sm antibodies (anti-Sm), methods for their production by continuous living cells in vitro, methods for their utilization in serological procedures for detecting the presence of the autoimmune disease lupus erythematosus (LE) in humans, and to the continuous cell lines used for the production of the monoclonal antibodies.

LE is an autoimmune disease affecting 0.1% of the female and 0.01% of the male population. One of the cardinal features of the disease is the production of various autoantibodies against the tissues of the patient. The most commonly found antibodies are specific for antigens known in this art as Sm, RNP, DNA, La, Ro ribosomes and lymphocytes. The corresponding antibodies are known as anti-Sm, anti-RNP, anti-DNA, etc. The amount of antibody present in a diseased host depends upon the individual patient, degree of treatment, and other unknown factors. The antibodies, with the exception of anti-Sm are found in patients afflicited with rheumatoid diseases other than LE, so that methods for the detection of antibodies other than anti-Sm do not provide specific detection of LE. It presently appears that anti-Sm only is not present in the sera of all LE victims although the percentage of LE victims carrying this antibody is very high—probably over 30%. Therefore, a specific test for anti-Sm in suspected LE patients is detected clinically by relatively crude and inexact techniques including:

1. a typical pattern of indirect immunofluorescence staining of tissues with anti-Sm;
2. reactivity with a crude preparation of Sm antigen compared to the reactivity of a known standard patient's sera in agar gel diffusion or in hemagglutination.

In accordance with this invention, new techniques have been developed for producing monoclonal anti-Sm. The anti-Sm produced can be utilized in a variety of valuable procedures. One of these is to test for the presence of anti-Sm in human sera, as a test for LE. Another is the preparation of pure Sm antigen which is useful in research. A particularly valuable utility for the monoclonal antibodies of this invention, one of several utilities which does not apply to the naturally occurring antibody as it occurs in human sera, is that they can be employed to produce unlimited amounts of standard anti-Sm reference preparations to which patient anti-Sm titer can be compared.

New techniques have been developed in accordance with this invention for producing monoclonal anti-Sm, more particularly for the propagation of new cell lines which are genetically stable, can be cultivated and subcultivated indefinitely, and produce large amounts of anti-Sm. The new cell lines are fused hybrids of myeloma cells from mice or rats and antibody producing cells from the spleen or lymph nodes of mice. Myeloma cells are malignant cells from primary tumors of bone marrow. Any combination of mice or rat source of myeloma and antibody producing cells is possible. Thus, rats can be the source of the myeloma cells and mice the source of the antibody producing cells. However, it is preferred that both cells be from the same species.

A particularly preferred embodiment of the monoclonal anti-Sm producing process is to utilize the combination of SP 2/0 Ag 14 mouse myeloma cells and spleen cells from MRL/MP-1pr/1pr mice.

The cell lines of this invention can be maintained substantially indefinitely in a composition comprising the continuous cell line in the known hypoxanthine-aminopterin-thymidine (HAT) medium. They can also be maintained in the same medium without the aminopterin. In fact, once the hybridoma cell line is established, it can be maintained on a variety of nutritionally adequate media.

The cells can be grown in vivo in histocompatible animals. These animals will accumulate large amounts of anti-Sm in their serum and ascites fluid. The expanding cell line can be frozen for storage and thawed when needed.

Prior to this invention, it was not known that monoclonal hybrid cells could be formed between anti-Sm producing cells and myeloma cells. Surprisingly, it has been found that such hybrid cell lines can be produced by fusing the cells, suitably in the presence of a fusion medium such as polyethylene glycol (PEG) to produce the hybrid and thereafter culturing the fused cells. The antibodies produced by the growing cell lines can be detected and collected by standard techniques.

Sm antigen is a known and well characterized antigen. It has been described in the literature and is readily recognized by those skilled in this art; see, for instance, Tan and Kunkel, J. Immunol. 96, 464 (1966) and Lerner and Steitz, Proc. Nat. Acad. Sci. USA 76, 5495 (1979). It appears to be largely but not exclusively nuclear. It is resistant to RNase, but partially sensitive to trypsin.

The scope of this invention includes serological methods for determining the presence of anti-Sm in human sera. Essentially, the processes of the invention comprise incubating or otherwise contacting the serum to be tested with monoclonal antibodies or with Sm antigen and detecting the presence of a reaction product. A convenient source for purified Sm antigen is to use the anti-Sm of this invention to isolate and purify the antigen from any convenient source. Those skilled in the art will recognize that there are many variations of these basic procedures. These include for example, RIA, ELISA, precipitation, agglutination, complement fixation and immunofluorescence. In the presently preferred procedures, the monoclonal antibodies are appropriately labeled and the labeled antibody is employed in a competition assay with anti-Sm present in the patient's serum. A convenient label for this competition assay is a radioactive isotope, particularly $^{125}I$. However, enzymes particularly peroxidase are also useful.

Anti-Sm can be chemically conjugated to or physically adsorbed on an insoluble particulate carrier. Useful adsorbents include, for example, lecithin-cholesterol and various polymer latices such as a polystyrene latex, polycarbonate, bentonite or charcoal. The anti-Sm is adsorbed on the adsorbent, mixed with the sera to be tested and the presence or absence of flocculation or clumping noted. Positive reactions give clumps while with negative reactions, the antibody coated particles remain homogeneously dispersed.

The antibody can be labeled with a radioactive element, an enzyme or a fluorescent material. The radiolabel can be detected by any of the currently available counting procedures. The preferred isotope labels are $^{14}C$, $^{131}I$, $^{125}I$ and $^{35}S$. The enzyme label can be detected by any of the currently utilized colorimetric, spectrophotometric, fluorospectro-photometric or gasometric techniques. The enzyme is combined with the antibody with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase, galactose oxidase plus peroxidase and acid phosphatase. Fluorescent materials which may be used include, for example, fluorescein, rhodamine and auramine.

Various labeling techniques are described in Morrison, Methods in Enzymology 32b, 103 (1974), Syvanen et al, J. Biol. Chem. 284, 3762 (1973) and Bolton and Hunter, Biochem J. 133, 529 (1973).

It has long been known that mice develop a LE like syndrome that includes the production of auto antibodies for nucleic acid containing cellular components. One of these antibodies, it has now been discovered, is indistinguishable from anti-Sm produced in the sera of humans afflicted with LE. This antibody occurs in a variety of lymphocyte sources such as bone marrow and peripheral blood. It is especially abundant in spleen and lymph nodes of mice. These lymphocyte sources can be used to obtain cells which, by fusion with myeloma cells from rats or mice, produce hybrid cell lines capable of producing unlimited amounts of anti-Sm. The basic process of this invention, therefore, comprises fusing antibody producing cells from a lymphocyte source in mice manifesting an LE like syndrome with myeloma cells from the same animal source or from rats to produce a fused cell hybrid, culturing the hybrid, and collecting the antibodies.

The prepare the spleen cells, the spleen is removed from the mouse and the cells are separated from the spleen in Dulbecco's Modified Eagle's Medium (DMEM). The cells are spun at 1500 RPM for five minutes. The supernatant is removed and the cells washed with fresh DMEM and again spun down.

The myeloma cells are grown in the following mediums:

500 ml RPMI 1640
5 ml HEPES (N-2-hydroxyethylpiperazine-N'-2-ethanesulfonic acid)
5 ml L-glutamine (200 mM solution)
50 ml calf serum
10 ml pen-strep
1 ml azaguanine The pen-strep is a 1:1 mixture of 5000 IU/ml penicillin and 500 mcg/ml streptomycin. RPMI 1640 is a standard growth medium from GIBCO. The calf serum is inactivated by heating at 56° C. in a water bath for 3–45 minutes. The final concentration of azaguanine is $8 \times 10^{-7}$M.

The cells are grown in 5% carbon dioxide to a cell density which does not exceed $7 \times 10^5$ cells/ml.

On the day before fusion, the cells are transferred to an azaguanine free medium, and on the day of fusion, the cells are washed once with DMEM and counted.

Hybridomas are formed by the fusion of short lived antibody producing cells and long lived myeloma cells. The product when the proper cells are fused, is a long lived cell line which secretes anti-Sm.

Because the parental myeloma cells have an unlimited life span in culture, it is necessary to have a system for selecting the desired hybrid cells from parents. The selecting system employed in this invention involves the use of the enzyme hypoxanthine-guanine-phosphoribosyl transferase (HGPRT). This enzyme is part of the purine salvage pathway in mammalian cells. These cells are also capable of synthesizing purines de novo. Under most conditions, both pathways probably operate to a certain extent. If a cell lacks HGPRT, the salvage pathway is blocked and purines must be manufactured from non-purine materials.

The chemical 8-azaguanine is an antimetabolite which is capable of masquerading as the purine guanine and replacing it in some of its normal reactions. Azaguanine is incorporated into DNA, interfering with the normal growth pattern and leading to cell death. Since azaguanine must be salvaged, any cell which lacks HGPRT activity cannot utilize azaguanine and will grow in its presence.

A selective system which operates on the same enzyme but in the opposite sense in that HGPRT positive cells are selected is described by J. W. Littlefield in Science, 145, 709 (1964). It is called HAT and contains hypoxanthine, aminopterin and thymidine (HAT medium). Aminopterin is an antimetabolite that prevents de novo purine synthesis and methylation of deoxyuridylate to form thymidylate. Hypoxanthine can serve as a salvagable purine in the event that aminopterin blocks de novo purine biosynthesis while thymidine bypasses the necessity for the methylation of thymidylate. Thus, in the presence of aminopterin, any cell with positive HGPRT activity will proliferate while cells with negative HGPRT activity will die.

In the hybrid system used for selection in accordance with this invention, the myeloma cells are resistant to azaguanine and susceptible to aminopterin, that is, they are HGPRT negative. Thus, they will die in the presence of aminopterin. The anti-Sm producing cells are HGPRT positive. By fusing the cells and growing them in HAT medium without azaguanine (HT medium), the successfully fused cells are selected because the myeloma cells which constitute the proliferating line can only grow where HGPRT activity is present and this activity must be supplied by the HGPRT positive cell line. The antibody producing HGPRT positive cell line are not killed in this medium. They will live for a time but will not proliferate.

Thus, by fusing the cells in a HAT medium, systems are produced in which the myeloma cells and anti-Sm producing cells can grow long enough to produce hybrid cells but in which only the hybrid cells can survive and proliferate.

In a typical fusion procedure of the invention, spleen and myeloma cells in a ratio of 2:1 together with DMEM are mixed together in a 15 ml centrifuge tube and spun at 1500 RPM for 10 minutes. The supernatant is removed. Next, 0.8 ml of 50% aqueous PEG at 37° C. is added and mixed with the pellet. One ml of DMEM is added at 37° C. The mixture is spun for 10 minutes at 1500 RPM and the supernatant removed.

PEG with molecular weights from 1000 to 2000 may be employed. The preferred material is PEG 1500 which is understood to have a molecular weight range of about 1430 to 1570.

The pellet is suspended to a total concentration of $1 \times 10^7$ cells/ml in DMEM with 4.5 g/l glucose supplanted with 10% NCTC 109 growth medium. (Microbiological Associates, Walkersville, Md.), 15% fetal calf serum, 10 mM HEPES, 1 mM sodium pyruvate, 2 mM l-glutamine, 50 ug/ml penicillin, 50 ug/ml amphotericin, $1 \times 10^{-4}$M hypoxanthine and $1 \times 10^{-6}$M thymidine. This is HT medium. Two drops of the mixture is added to each well of a 96 well plate.

The cells are incubated for one day and then one drop of the above medium supplemented with $8 \times 10^{-7}$M aminopterin is added. This is HAT medium which functions as the selective medium as described above. The wells are incubated for four days and one-half of the supernatant is removed. This is replaced with two drops of HAT medium. This process is repeated on the seventh day. The hybridomas may be cultured thereafter on HT medium. The clones become macroscopic after 10 to 20 days.

Two to three weeks after fusion, the culture supernatants are tested for antibody activity using a rapid screen procedure in which one gram of rabbit thymus extract (Pel-Freez, Rogers, Ark.) is suspended in 10 ml phosphate buffered saline (PBS) and 50 ul of the solution added to wells of a flat bottom polystyrene plate. This step and all subsequent steps are carried out at 4° C. At the end of 12 hours, the plates are washed once with PBS and the remaining non-specific binding sites blocked by exposure to 1% bovine serum albumin (BS) with 0.1% sodium azide for 12 additional hours. The plate is then washed three times with PBS and 50 ul of culture supernatant added and incubated overnight. After another wash with PBS, the antibodies are bound by the addition of 20,000 CPM of $^{125}$I-protein-A (Pharmacia) in 50 ul PBS. The mixture is incubated for 12 hours and the plate washed six times with PBS. In this manner, only Protein A binding antibodies are obtained. Autoradiography is performed with Kodak RPR x-ray film and an intensifying screen (Cronex Lighting Plus, DuPont) mounted on the bottom of the plate. Positive wells appear as dark spots against a faint background.

Typically, of about 200 hybrid culture supernatants examined, about 20 appear positive by this rapid screening assay.

To further evaluate the positive culture, HeLa cells are labeled for about twelve hours with $^{32}$P-orthophosphate. A cell sonicate is prepared and antibody is added. The antigen-antibody complex is precipitated with staphlycoccus Protein A (Calbiochem). The resultant immunoprecipitate is run on 10% acrylamide 7 molar urea gel to determine the exact molecular targets of the hybridoma antibodies. Gels are exposed to x-ray film as described above. Typically, of 20 cells screened in this manner, one is positive for anti-Sm activity.

Cells from the well showing anti-Sm activity are subcloned on 0.5% agar containing medium to insure monoclonal growth. Macroscopic clones are plucked, for example, with a Pasteur pipette and grown in HAT medium. Positive cultures may be expanded and frozen for future use. Alternatively, they may be injected into the peritoneal cavities of histocompatable mice, specifically Pristane treated (BALB/c×A)F, mice to generate ascites.

Antibody from the ascites fluid may be isolated by precipitation with 45% saturated ammonium sulfate followed by dialysis against PBS. The antibody may be further purified by IgG class specific elution from a Protein A Sepharose column by the procedure of Ey et al, Immunochemistry, 15, 429, (1978). The fractions may be analysed by Ouchterlony analysis against class specific goat anti-mouse immunoglobulin. The anti-Sm are of the IgG2a class.

The cell lines can be frozen for future use and thawed when needed.

In one method of freezing, $5 \times 10^6$ cells are pelleted from the growth medium by spinning and suspended in 1 ml of a mixture of 90% fetal calf serum and 10% dimethyl sulfoxide. The suspension is slowly frozen at $-70°$ C. in a styrofoam insulator. The frozen cells are stored in a liquid nitrogen freezer.

For thawing, the vials containing the frozen cells are warmed quickly to 37° C. and poured in 10 ml of PBS. The pellet is collected by spinning, resuspended in 10 ml of HT growth medium at 37° C., and incubated. The cultures are expanded in 5% carbon dioxide in the following medium:
50 ml RPMI 1640
5 ml HEPES
5 ml L-glutamine
50 ml calf serum
10 ml pen-strep As indicated above, the continuous cell line can be propogated in vivo in ascites fluid and the high concentration of anti-Sm which accumulates treated to isolate the antibody. This may be accomplished by the following series of steps:
1. Prime (BALB/c×A)F, mice with 0.5 ml Pristane (2,6,10 14 tetramethylpentadecane) I.P. at least 5 days before injecting hybrid cells.
2. Inject 1 to $5 \times 10^6$ hybrids I.P. in 0.5 ml saline.
3. Tap the mice when ascites develop (1-3 weeks).
4. Spin or filter the ascites fluid.
5. Precipitate the gamma globulin fraction of the ascites at least once with 45% saturated ammonium sulfate.
6. Spin at 3000 RPM for 15 minutes.
7. Resuspend and dialyze against PBS at 4° C.
8. Store the dialysate containing the antibodies under sterile conditions or with 0.1% azide in the refrigerator.

If a highly purified sample of monoclonal antibody is desired, this can be accomplished by IgG class-specific elution from a protein A-Sepharose column as suggested above. Other procedures such as ion exchange chromatography or gel filtration can be used.

Anti-Sm produced by the continuous hybrid cell lines of this invention are substantially identical with the antibodies from the spleen of MRL/L mice exhibiting a LE like syndrome and from the sera of LE patients. This is established by a comparative study using the monoclonal antibodies of this invention, sera from patients with LE as defined by the American Rheumatism Association and sera from MRL mice exhibiting the LE syndrome.

In the experiment, serum from a selected mouse is precipitated with $^{32}$P-labeled sonicates of HeLa cells. The precipitate is extracted with phenol and fractionated at room temperature on 10% polyacrylamide (27:1 acrylamide/bisacrylamide) gels in 7M urea/45 mM Tris borate, pH 8.3/1.25 mM EDTA.

Spleen cells from the same mouse are fused with myeloma SP 2/0 Ag 14 cells to produce hybrid cell lines as described above. After screening by solid phase RIA, the individual solid phase hybridoma products are examined by immunoprecipitation as described for the mouse serum.

Sera from patients is examined in the same way as a serum from the mouse. All three sources provide electrophoretic patterns of small nuclear RNAs which are essentially similar. Bands for U1, U2, U4, U5 and U6 are observed with antibodies from all three sources.

U1, U2, U4, U5 and U6 are small nuclear ribonucleic acids (snRNAS) which are well known and characterized. They are widely distributed in human and animal cells.

The monoclonal antibodies of this invention are characterized by their ability to react specifically with Sm and to precipitate U1, U2, U4, U5 and U6 containing ribouncleoprotein particles.

Monoclonal anti-Sm labeled with a radioactive isotope can be used in a competition assay to determine the anti-Sm activity of human sera. In the test, rabbit thymus extract is absorbed in plastic microtiter plates. The absorbed extract is then exposed to the sera under test, for example, sera from several patients or sera from the same patient taken at different times. After incubation for a suitable period, the sera is removed, the plates washed with PBS and then incubated with an excess $^{125}I$ labeled monoclonal anti-Sm. Since the unlabeled antibody inhibits binding of the labeled antibody, the test sera with the highest concentration of antibody will permit binding of the lowest amount of labeled antibody. The amount of bound, labeled antibody can be determined with a counter.

Indirect immunofluorescence on Vero cells can be employed to compare monoclonal anti-Sm with antibody from LE patients. Both antibody preparations exhibit a classical anti-Sm staining pattern; diffuse nuclear speckling excluding the nucleoli and faint cytoplasmic staining.

For this immunofluorescence study Vero (African green monkey kidney) cells are cultured overnight on coverslips and fixed with methanol and acetone. Ten ul of monoclonal or patient antibody are spread on each coverslip and allowed to incubate for 1 hour at 37° C. The coverslips are washed six times in PBS and biotinyl Protein A followed by FITC-Aviden is added. The mixture is incubated and washed. The coverslips are then mounted in microscope slides with polyvinyl alcohol and glycerol and examined.

For obtaining photographs of the stains, a Zeiss standard binocular 14 fluorescence microscope equipped with a mercury lamp and vertical illuminator with 450 to 490 nm excitation and 520 nm barrier filters may be used. Photographs are taken with high speed Ektachrome (ASA 400) film using four minute exposure times.

These procedures as well as the competitive assay using anti-Sm labeled with an enzyme are illustrated in the following non-limiting examples.

EXAMPLE 1—PREPARATION OF SPLEEN CELLS

Automimmune mice whose sera are positive for the desired antibody, are killed by cervical dislocation and their spleens removed under aseptic conditions and placed in a Petri dish containing Dulbecco's Modified Eagle's Medium (DMEM). A spleen cell suspension is made by teasing the cells from the spleen using a syringe filled with DMEM and a pair of forceps. The suspension is transferred to a 15 ml tube and the cells pelleted by centrifugation at 1500 RPM for 5 minutes in a clinical centrifuge. The supernatant is removed and the cells washed by resuspending them in 10 ml of DMEM. The cells are counted, spun and resuspended to $2 \times 10^7$ cells/ml—usually $10^8$ cells/spleen.

EXAMPLE 2—PREPARATION OF MYELOMA CELLS

Myeloma cells are grown in 8-azaguanine containing medium until the day before the fusion when they are placed in media lacking 8-azaguanine. Enough cells are grown such that during the fusion, the myeloma/spleen cell ratio is 1:3, i.e. $3.3 \times 10^7$ myeloma cells will be needed to fuse with $10^8$ spleen cells.

The myeloma cells are centrifuged, resuspended in 5 ml of DMEM, counted, and $3.3 \times 10^7$ cells added to the tube containing the spleen cells.

EXAMPLE 3—FUSION OF CELLS

The mixture of spleen and myeloma cells is centrifuged at 1500 RPM for 10 minutes and the supernatant removed. With the cell pellet still intact, 0.8 ml of a 40% solution of polyethylene glycol 1500 (PEG) 60% DMEM which has been kept in a 5% $CO_2$ 37° C. incubator overnight, is added via a pipette over 1 minute. During this time, and the next minute, the pipette tip is used to stir the cell pellet while the tube is held in the palm of the hand to maintain an elevated temperature. One ml of DMEM warmed to 37° C. is then added over each of the next 2 minutes followed by 10 ml over the next 2 minutes.

The mixture is then spun at 1500 RPM for 10 minutes, the supernatant removed, the cells suspended to $10^7$ cells/ml in medium containing hypoxanthine and thymidine, 2 drops of said suspension added to wells of 96 well plates, and the culture placed in an 8% $CO_2$ 37° C. incubator. One drop of HAT medium is added the next day and every 3 days. Wells with clones are usually ready to be screened in 2 weeks.

EXAMPLE 4—SCREENING PROCEDURE

A stock solution of rabbit thymus extract (RTE), which is known to contain antigens with which the desired antibodies will react, is prepared by suspending 1 gm of dried extract in 10 ml of phosphate buffered saline (PBS).

A 1:10 dilution of this stock solution is added to 96 well plates and incubated for 1 hour. This and all subsequent incubations are at 4° C. 1% bovine serum albumin in PBS is then incubated for 1 hour to block any non-RTE bound sites. The plates are washed twice with PBS and 50 ul of test culture supernatant containing the putative antibody is added to the wells, incubated for 8 hours, and washed away. 20,000 cmp of $^{125}I$-protein A in 50 ul is then added to the wells and the presence of a $^{125}I$-protein A/antibody/RTE complex detected by mounting the plate on a piece of x-ray film. Upon developing the film, positive culture supernatant wells will appear as dark spots.

Antibodies from clones found to be active by this simple but nonspecific assay are then assayed for their ability to react with discrete molecular targets. Here, HeLa cells are labeled with $^{32}P$, a cell extract prepared, 200 ul of culture supernatant added, antigen-antibody complexes precipitated with staphlococcus containing protein A, the material run out on a 10% acrylamide 7M urea gel and autoradiography performed overnight. Characteristic banding patterns observed for particular antigens enable the exact molecular target of the antibodies to be ascertained.

EXAMPLE 5—PURIFICATION OF MONOCLONAL ANTIBODIES

The simplest way to substantially purify and concentrate the antibody is by precipitation with ammonium sulfate. A volume of saturated ammonium sulfate is slowly added to the antibody containing solution until the ammonium sulfate concentration has reached 45% by which point the antibody will precipitate. The solution is then centrifuged at 3000 RPM for 20 minutes to pellet the precipitate, the pellet resuspended in PBS and the remaining ammonium sulfate removed by dialysis against PBS.

EXAMPLE 6—LABELING ANTI-Sm WITH IODINE ISOTOPE

To a 12×75 mm glass test tube containing 50 ug of anti-Sm antibody in 100 ul of PBS are added 6 ul of lactoperoxidase and 15 ul of $5\times10^{-5}$M potassium iodide. In a radiation fume hood, 0.2 uCi of $^{125}$I is added and the tube incubated for 5 minutes at 30° C. The reaction is quenched with 1 ml of cold PBS and the solution dialysed overnight versus PBS to remove uncoupled $^{125}$I.

EXAMPLE 7—USE OF RADIOLABELED ANTI-Sm IN A COMPETITIVE RADIOIMMUNOASSAY TO DETECT ANTI-Sm ACTIVITY IN PATIENT'S SERA

Flexible polyvinyl 96 well plates are coated with a 1:125 dilution of RTE, incubated at 4° C. for 1 hour, the unbound sites blocked with 1% BSA in PBS, and washed twice with PBS. Duplicate wells are then incubated with dilution in PBS, of patient sera, for 8 hours and washed. Next, a constant amount of $^{125}$I-labeled monoclonal anti-Sm antibody—20,000 cpm in 50 ul of PBS, is incubated for 8 hours and the plates washed 5 times. Wells are cut out and counted in a gamma counter.

Inhibition of $^{125}$I counts is consistent with the presence of anti-Sm in the patient's sera as patient anti-Sm competes with $^{125}$I-anti-Sm monoclonal antibody for the available binding sites. The patient's antibody titer can be found by determining the dilution at which there is no inhibition of $^{125}$I-anti-Sm binding.

EXAMPLE 8—LABELING ANTI-Sm WITH AN ENZYME

Procedure of Avrameas and Ternyck, *Immunochemistry* (1971) 8 pp. 1175–1179.

10 mg of horse radish peroxidase is dissolved in 0.2 ml of 0.1M phosphate buffer pH 6.8 containing glutaraldehyde, and allowed to stand at room temperature for 18 hours. The glutaraldehyde is removed by dialysis against normal saline and the solution is made up to 1 ml in saline. 5 mg of antibody, prepared from a salt cut of ascites fluid, in 1 ml of saline added followed by the addition of 0.1 ml carbonate buffer pH 9. The solution is mixed and allowed to stand at 4° C. for 24 hours. The antibody is precipitated with 45% saturated ammonium sulfate, to remove uncoupled enzyme, dialyzed against PBS, and stored at −70° C. in PBS with 30% glycerol.

EXAMPLE 9—USE OF LABELED ANTI-Sm IN A TEST FOR ANTI-Sm IN PATIENT'S SERA

Flat bottom polystyrene 96 well plates are coated with a 1:125 dilution of RTE stock solution at 4° C. for 1 hour. Duplicate wells are incubated with patient sera diluted in PBS containing 0.05% Triton X-100 for 8 hours, washed once, incubated with appropriately diluted peroxidase coupled anti-Sm in PBS/0.05% Triton X-100 for 8 hours and washed 3 times.

To test for the degree of competition between patient sera and peroxidase coupled antibody, the substrate OPD (o-phenylenediamine) is used. When OPD is cleaved by the peroxidase, a yellow-orange color appears. The intensity of the color is proportional to the amount of bound peroxidase labeled antibody so that a patient serum containing anti-Sm would prevent binding of peroxidase-monoclonal anti-Sm to the RTE and result in little color accumulation.

20 mg of OPD is dissolved in 24.3 ml 0.1M citric acid and 25.7 ml 0.2M sodium dibasic phosphate. 20 ul of 30% $H_2O_2$ is added to initiate the reaction. 250 ul of substrate solution is added to the wells and incubated for thirty minutes at which time 50 ul of 6N HCl is added to quench the reaction. Results from the ELISA are tabulated by spectrophotometric determinations of absorbance using a spectrophotometer equipped to read 96 well plates.

EXAMPLE 10—LABELING OF ANTI-Sm WITH BIOTIN FOR USE AS A FLUORESCENT PROBE FOR Sm

The antibody is dialyzed against 0.1M $NaHCO_3$ pH 8.2–8.6 and adjusted to 1 mg/ml. To each ml is added 120 ul of DMSO containing 120 ug of biotin succinimide ester. The mixture is mixed and allowed to incubate at room temperature for 4 hours and then dialyzed against PBS to remove uncoupled biotin.

EXAMPLE 11—USE OF BIOTIN LABELED ANTI-Sm IN A TEST FOR Sm

Vero cells grown on coverslips are fixed with cold acetone and methanol. 10 ul of appropriately diluted biotinyl-anti-Sm are spread on the coverslip and incubated at 37° C. for 30 minutes. Unbound antibody is removed by dipping the coverslips in PBS. Next, an appropriate 10 ul dilution of fluorescein coupled avidin is spread and incubated and then washed. The coverslip is mounted onto a microscope slide with a drop of polyvinyl alcohol. The slide is examined under a fluorescent microscope for the speckled nuclear but non-stained nucleolar pattern characteristic of Sm.

EXAMPLE 12—USE OF ANTI-Sm TO PRODUCE PURE Sm

Sm is an antigen on a series of particles composed of RNA and protein. To purify the particles, an extract containing Sm is passed over a column composed of monoclonal anti-Sm covalently coupled to Sepharose. Unbound material is washed from the column with PBS and purified Sm is then specifically eluted from the column with 2M lithium chloride.

EXAMPLE 13 PROOF THAT ANTI-Sm IS OF THE IgG2a CLASS

Culture supernatant from the anti-Sm hybridoma is concentrated 10 fold by precipitation with saturated ammonium sulfate. The material is then subjected to Ouchterlony (immunodiffusion) analysis against goat antisera directed against individual mouse immunoglobulin classes—goat anti-mouse IgG1, IgG2a, IgG2b, IgG3, IgM, IgA, IgD and IgE. Only the anti-IgG2a will yield a precipitin line proving that the anti-Sm monoclonal antibody is of the IgG2a class.

A culture of the living mouse-mouse hybridoma cell line of this invention was deposited on Mar. 11, 1981 with the American Type Culture Collection, 12301 Parklawn Drive, Rockville Md. 20852 and was accorded accession number HB8050.

What is claimed is:

1. A continuous cell line which produces anti-Sm antibodies of the IgG class in vitro in hypoxanthineaminopterin-thymidine medium and comprises a fused cell hybrid of cells from the spleen or lymph node of mice manifesting a lupus erythematosus-like syndrome and myeloma cells from mice or rats.

2. A continuous cell line as in claim 1 wherein the hybrid is a clone resulting from the fusion of spleen or lymph node cells from mice and myeloma cells of mice.

3. Murine monoclonal anti-Sm antibodies of the IgG2a class characterized by reacting specifically with Sm antigen and the ability to precipitate the small nuclear ribonucleic acids U1, U2, U4, U5 and U6.

4. The anti-Sm antibodies of claim 3 labeled with a detectable radioisotope, enzyme or fluorescent label.

5. A serological method for determining the presence of Sm antibody in human sera which comprises incubating the serum to be tested with an excess of Sm antigen, incubating resulting mixture with labeled monoclonal Sm antibody and determining the extent to which the labeled antibody is inhibited from reacting with the Sm antigen.

6. A method as in claim 5 wherein the monoclonal antibody is labeled with a chemical which fluoresces when exposed to ultraviolet light.

7. A method as in claim 6 wherein the chemical is selected from the group consisting of fluorescein, rhodamine and auramine.

8. A method as in claim 5 wherein the monoclonal antibody is labeled with an enzyme.

9. A method as in claim 8 wherein the enzyme is selected from the group consisting of peroxidase, $\beta$-glucuronidase, $\beta$-D-glucosidase, $\beta$-D-galactosidase, urease, glucose oxidase plus peroxidase, galactose oxidase plus peroxidase and acid phosphatase.

10. A method as in claim 5 wherein the monoclonal antibody is labeled with a radioactive element.

11. A method as in claim 10 wherein the radioactive element is selected from the group consisting of $^{14}C$, $^{125}I$, $^{131}I$ and $^{35}S$.

* * * * *